United States Patent [19]

Crudden

[11] Patent Number: 5,186,855
[45] Date of Patent: Feb. 16, 1993

[54] PROCESS FOR PRODUCING A SYNTHETIC DETERGENT SOAP BASE FROM N-ACYL SARCOSINE

[75] Inventor: Joseph J. Crudden, Hudson, N.H.
[73] Assignee: W. R. Grace & Co.-Conn., New York, N.Y.
[21] Appl. No.: 670,799
[22] Filed: Mar. 18, 1991
[51] Int. Cl.$^5$ ................................................. C11D 9/30
[52] U.S. Cl. .................................. 252/117; 252/108; 252/118; 252/122; 252/546; 252/DIG. 5; 252/DIG. 16
[58] Field of Search ............... 252/108, 117, 118, 122, 252/546, DIG. 5, DIG. 16

[56] References Cited

U.S. PATENT DOCUMENTS

| | | | |
|---|---|---|---|
| 3,879,309 | 4/1975 | Gatti et al. | 252/117 |
| 4,092,259 | 5/1978 | Prince | 252/117 |
| 4,273,684 | 6/1981 | Nagashima et al. | 252/546 |
| 4,754,874 | 7/1988 | Haney | 206/77.1 |
| 4,758,370 | 7/1988 | Jungermann et al. | 252/108 |
| 4,812,253 | 3/1989 | Small et al. | 252/132 |
| 4,919,838 | 4/1990 | Tibbetts et al. | 252/117 |
| 4,954,282 | 9/1990 | Rip et al. | 252/117 |
| 4,975,218 | 12/1990 | Rosser | 252/108 |
| 4,980,078 | 12/1990 | Verite | 252/118 |

Primary Examiner—Paul Lieberman
Assistant Examiner—Bradley A. Swope
Attorney, Agent, or Firm—Kevin S. Lemack; William L. Baker

[57] ABSTRACT

A method of producing a synthetic detergent soap base, comprising neutralizing n-acyl sarcosine at an elevated temperature with a fatty acid salt to the desired pH, and allowing the mixture to cool. The resulting product is non-irritating and non-drying, and exhibits apparent skin substantivity and pleasant skin feel.

4 Claims, No Drawings

PROCESS FOR PRODUCING A SYNTHETIC DETERGENT SOAP BASE FROM N-ACYL SARCOSINE

BACKGROUND OF THE INVENTION

1. Field of the Invention

This invention relates to a process of making a synthetic detergent soap base from N-acyl sarcosine.

2. Description of the Prior Art

The use of sarcosinate surfactants, and in particular, N-acyl sarcosinates in the manufacture of soap is well known. Typically, the sarcosinate is used in the form of its sodium, potassium or ammonium salt solution. N-acyl sarcosinates are produced commercially by the Schotten-Baumann reaction of the sodium salt of sarcosine with the appropriate fatty acid chloride under carefully controlled conditions:

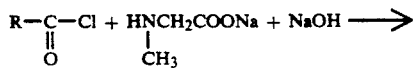

where R is typically a fatty acid of chain length $C_{10}$ to $C_{18}$, commonly made from lauric, coconut, palmitic, myristic or oleic acid. After the reaction is complete, the crude sodium salt is acidified to liberate the free fatty sarcosinic acid which is separated from the aqueous by-products. It then is neutralized to a salt form. Sarcosinates such as sodium lauroyl sarcosinate, sodium cocoyl sarcosinate and sodium myristoyl sarcosinate are commercially available under the trademark HAMPOSYL ® by W. R. Grace & Co.-Conn., as 30% active solutions in water. To produce soap bars, much of the water is removed, which may require heating the mixture to temperatures in the vicinity of 150C.

Such sarcosinates are used, for example, in the skin cleansing compositions disclosed in U.S. Pat. No. 4,812,253. There it is disclosed that surfactants such as anionic acyl sarcosinates are present in the cleansing composition at a level of 20-70%, 20-50% in the case of soaps. In addition, sodium lauroyl sarcosinate is disclosed as being a preferred secondary surfactant together with sodium coco glyceryl sulfonate as a primary mild surfactant. The soap is disclosed as being made in situ from free fatty acids and a base selected from magnesium hydroxide, potassium hydroxide, sodium hydroxide and triethanolamine. Preferred fatty acids are mixtures of stearic and lauric acids having a ratio of from 2:1 to 1:1.

U.S. Pat. No. 4,754,874 to Haney discloses a transparent, mild, low pH soap bar and package therefor. The soap formulation disclosed includes sodium stearate and sodium cocoyl sarcosine, but no method of formulation is taught.

U.S. Pat. No. 4,954,282 to Rys et al. discloses skin cleaning compositions containing major amounts of acyl isethionates and at least one co-active surfactant, including sarcosinates.

SUMMARY OF THE INVENTION

The problems of the prior art have been solved by the instant invention, which provides a process for the production of a synthetic soap base with an easily adjustable pH. Surprisingly, it has been found that N-acyl sarcosine can be used as a solvent for a fatty acid salt. Accordingly, the instant process involves neutralizing N-acyl sarcosine by dissolving a fatty acid salt in the heated acid until the desired pH is obtained. The desired pH can be retained while varying the ratio of the fatty acid salt to n-acyl sarcosine by adding acid or base. By using sarcosine acid rather than the salt, no excess water needs to be eliminated, and easy processability, easy control of pH, and decreased production costs are realized. The resulting product is non-irritating and non-drying, and exhibits apparent skin substantivity and pleasant skin feel.

DETAILED DESCRIPTION OF THE INVENTION

Fatty acid salts having carbon chain lengths from about $C_8$ to about $C_{18}$ are functional in the instant invention. Preferred fatty acid salts are salts of stearic, myristic, palmitic and lauric acids, with salts of stearic acid being especially preferred. Suitable salifying ions include those selected from alkali metals and alkali earth metals, preferably sodium and potassium. For purposes of illustration, sodium stearate will be referred to except where specified otherwise, although it should be understood that other fatty acid salts are within the scope of the instant invention.

Suitable n-acyl sarcosines in the instant invention include lauroyl sarcosine, cocoyl sarcosine, myristoyl sarcosine, oleoyl sarcosine and stearoyl sarcosine, with lauroyl sarcosine being preferred.

The instant method comprises neutralizing the n-acyl sarcosine by dissolving the fatty acid salt in the sarcosine until the desired pH is reached. The preferred pH is from about 4.5 to about 9.5, with a pH between about 5 and about 7 being especially preferred. A pH below about 4.5 is functional, but results in a bar that is very soft. A pH above about 9.5 deleteriously affects the foaming of the product. The fatty acid salt is easily dissolved in the sarcosine at an elevated temperature, such as a temperature of about 65° C. to about 140° C., preferably about 75° C. to about 100° C. At temperatures below about 65° C., a solid tends to form. At temperatures above about 100° C., decomposition of the fatty acid salt tends to occur, although the salt dissolves faster in the sarcosine. Thus, if temperatures higher than about 100° C. are used, it is preferred that the temperature be quickly lowered upon dissolution of the salt. When the homogenous liquid is allowed to cool to about room temperature, it solidifies to a hard soap-like material which functions adequately as a soap but is mild, non-drying and produces a pleasant skin feel. The material can be easily molded as it cools but also may be remelted. This surprising characteristic will allow production of soap bars on a commercial scale by the conventional press molding technique.

Other surfactants may be added to the formulation, such as isethionates, especially acyl isethionates including sodium cocoyl isethionate. The acyl isethionates may render the soap bar brittle. In such a case, the brittleness can be controlled by the addition of amines, such as isopropyl amine. In addition, other conventional soap additives, including but not limited to glycerols or EDTA solutions may be dissolved in the system without materially affecting its processability. It will be understood by those skilled in the art that other conventional additives, including perfumes, coloring agents, binders, skin feel and mildness aids, etc. may also be added.

The desired pH of the mixture can be retained while varying the ratio of the fatty acid salt to n-acyl sarcosine by adding acid or base. Suitable acids include sulfuric, citric, hydrochloric, lactic, lauric, etc. Suitable bases include sodium and potassium hydroxide, etc. Those skilled in the art will recognize that the addition of an acid or base to the system results in an exothermic reaction, and will affect the temperature thereof accordingly.

The instant invention will be better understood by referring to the following specific but non-limiting examples. It is understood that said invention is not limited by these procedures which are offered merely as illustrations; it is also understood that modifications can be made without departing from the spirit and scope of the invention.

EXAMPLE 1

40 grams of N-cocoyl sarcosine was heated in a beaker to a temperature between 80° C. and 100° C. on a stirrer hotplate. Sodium stearate powder (Witco C1) was gradually added with constant stirring and allowed to dissolve. The pH of the system was periodically checked by dipping a spatula in the liquid and transferring a few drops of the liquid to a beaker of distilled water which contained a pH probe and Was agitated by a magnetic stirrer. The pH of the aqueous system was monitored until a stable value was obtained. The initial pH value before addition of any stearate was approximately 2. With the addition of sodium stearate the pH gradually rose and, after the addition of approximately 48 grams, the desired pH of 6.5 was obtained. The resulting liquid was poured into a mold and allowed to set. When the temperature returned to ambient the mold was opened. The resulting product was a firm soap-like material which produced copious foam and a pleasant skin feel.

EXAMPLE 2

40 grams of n-lauroyl sarcosine was heated as before and 20 grams of n-cocoyl isethionate was gradually added and allowed to dissolve. Approximately 48 grams of sodium stearate was added as before until a pH of about 6.5 was obtained The clear liquid was formed into a bar by molding as in Example 1. The resulting material produced greater flash foam and was more brittle than the product of Example 1.

What is claimed is:

1. A method of producing synthetic detergent soap base comprising dissolving in a composition consisting essentially of an N-Acyl sarcosine selected from the group consisting of lauroyl sarcosine, cocoyl sarcosine, myristoyl sarcosine and oleoyl sarcosine an effective amount of a fatty acid salt to reach a pH of from about 4.5 to about 9.5, thereafter optionally adding at least one other surfactant and one or more conventional soap additives.

2. The method of claim 1 wherein said N-Acyl sarcosine is neutralized to a pH of from about 5 to about 7.

3. The method of claim 1 wherein said fatty acid salt is selected from the group consisting of salts of lauric, myristic, palmitic and stearic acid.

4. The method of claim 1 wherein the fatty acid salt is sodium laurate.

* * * * *